United States Patent
Lewis et al.

(10) Patent No.: US 7,533,673 B2
(45) Date of Patent: May 19, 2009

(54) SURGICAL DRAPE WITH PATIENT RETRAINING/POSITIONING DEVICE

(75) Inventors: Andrea L. Lewis, Mount Pleasant, SC (US); Uyles W. Bowen, Canton, GA (US); Gwendolyn E. Simpson, Riverdale, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 127 days.

(21) Appl. No.: 11/021,557

(22) Filed: Dec. 23, 2004

(65) Prior Publication Data

US 2006/0137693 A1 Jun. 29, 2006

(51) Int. Cl.
*A61B 19/00* (2006.01)
*A61B 19/08* (2006.01)
*A61F 5/37* (2006.01)

(52) U.S. Cl. .............. 128/849; 128/850; 128/851; 128/852; 128/853; 128/854; 128/855; 128/872; 128/873; 128/874; 128/875; 128/876

(58) Field of Classification Search .............. 128/849, 128/850, 852, 853, 855, 854, 851, 872, 873, 128/874, 875, 876
See application file for complete search history.

(56) References Cited

U.S. PATENT DOCUMENTS

| | | | |
|---|---|---|---|
| 2,927,581 A | 3/1960 | Queen | |
| 3,182,656 A | 5/1965 | Pyne | |
| 3,424,153 A | 1/1969 | Lewis, Jr. | |
| 3,667,458 A | 6/1972 | Krebs | |
| 4,730,609 A * | 3/1988 | McConnell | 128/853 |
| 4,742,821 A | 5/1988 | Wootan | |
| 4,903,710 A * | 2/1990 | Jessamine et al. | 128/849 |
| 5,010,899 A | 4/1991 | Thompson | |
| 5,040,546 A | 8/1991 | Deluhery | |
| 5,168,587 A | 12/1992 | Shutes | |
| 5,361,780 A * | 11/1994 | Kellan | 128/849 |
| 5,468,231 A | 11/1995 | Newman et al. | |
| 5,490,524 A * | 2/1996 | Williams et al. | 128/849 |
| 5,778,891 A * | 7/1998 | McMahan | 128/849 |
| 5,988,172 A * | 11/1999 | Sosebee | 128/849 |
| 6,314,959 B1 | 11/2001 | Griesbach et al. | |

* cited by examiner

*Primary Examiner*—Patricia Bianco
*Assistant Examiner*—Tarla Patel
(74) *Attorney, Agent, or Firm*—Dority & Manning P.A.

(57) ABSTRACT

A surgical drape for use during surgery on a patient includes a sheet configured for covering at least a portion of the patient during the surgery. At least one pair of straps are configured on an underside of the sheet and extend in generally opposite directions laterally beyond sides of the sheet. The straps have a sufficient length so as to extend down below the support surface upon which the patient rests and engage with each other below the support surface, or with structure alongside the support surface, in order to restrain the patient in a desired position on the support surface.

18 Claims, 7 Drawing Sheets

SURGICAL DRAPE WITH PATIENT RETRAINING/POSITIONING DEVICE

BACKGROUND

Various types of surgical drapes are known and used to keep a surgical site on a patient sterile during a surgical procedure. Traditionally, surgical drapes were linen or woven cloth, and were sterilized after each use for reuse. More recently, disposable sterile drapes have been introduced, in which a nonwoven paper or fabric forms a substantial part of the drape. A reinforcement area is often placed around a fenestration or an edge of disposable surgical drapes to provide structural strength and to absorb bodily fluids from the surgical site. Many disposable drapes also include a number of layers of different materials for the drape area and reinforcement area, with each layer providing a different property to the drape. For example, spunbond fabrics, meltblown fabrics, and polymer films have been used as layers in disposable drapes.

For a vast majority of surgical procedures, it is imperative that the patient remain still during the procedure. In many situations, the patient is completely sedated and the risk of patient movement during the procedure is minimal. However, there are numerous situations where the patient is only mildly sedated, or local anesthesia has been rendered, and the risk of patient movement is significantly increased. In such situations, it has been a practice in the medical field to restrain or position the patient on the surgical table with external devices. For example, a common practice is to use bed linens under the surgical drape to tie or otherwise secure the patient's limbs to the operating table. This method, however, still allows for an unacceptable amount of patient movement, and the bundled linens are often bulky and cumbersome. The linens are not disposable and must be thoroughly cleaned after the procedure.

U.S. Pat. No. 5,168,587 describes a patient positioning device for mobility impaired patients utilizing a corset adapted to be positioned around the torso of the patient. The corset is coupled to a flexible strap that is routed to a drive assembly located beneath the bed's mattress. The patient can be rotated by pulling in on one strap with the drive assembly while paying out the other strap. This type of positioning device would not be useful in an operating room for restraining a patient during a surgical procedure.

EP 0443174 describes a portable positioning device for restraining a patient in a lateral decubitus position of a table. The device includes rigid support walls and back support, and a flexible strap for holding the patient against the wall members. The device is placed on the table, and the patient is positioned on the table in a lateral decubitus position with their back against the back support. The strap is then wrapped around the patient's waist and pulled tight enough to secure the patient against the back support. This type of "above table" restraining device would not be practical for securing patients during a surgical procedure.

A need exists in the art for a more versatile surgical drape that may also be used to effectively restrain a patient against movement during a surgical procedure, or to secure a patient in a desired position for the procedure.

SUMMARY

Various features and advantages of the invention will be set forth in the following description, or may be obvious from the description, or may be learned from practice of the invention.

The present invention provides a surgical drape for use during surgery of a patient. The drape has a sheet configured for covering at least a portion of the patient during the surgical procedure. In a particular embodiment, at least one pair of straps are configured on an underside of the sheet, the straps extending in generally opposite directions laterally beyond sides of the sheet. The straps have a sufficient length so as to extend down below a support surface upon which the patient is resting, for example an operating table. The straps are intended to restrain the patient in a desired position on the support surface, and to aid in preventing inadvertent patient movement during the procedure. In one configuration, the straps are configured to pass below the support surface and attach together, thereby securing the patient against the support surface. In this regard, any manner of conventional attaching device is provided on one or both ends of the straps for securing the straps together. For example, the strap ends may be secured together by hook-and-loop material, adhesive, mechanical fasteners, and so forth. The attaching device may simply include tying the ends of the straps together. It should be appreciated that the invention is not limited by the device or means by which the straps are secured to each other.

In an alternate embodiment, the straps are configured to restrain the patient by attaching to one or more structural components of the support surface, such as the legs or understructure of an operating table. In this regard, any manner of attaching device may be provided on the ends of the straps. For example, an adhesive may be provided on the strap ends for pressing and adhering the ends to the support surface structure. A mechanical clip, fastener, or other device may also suffice. The ends of the straps may simply be wrapped and tied to the support surface structure.

The straps are not limited to any size, length, shape, or material. For example, the straps may be formed of the same material as the base sheet, or a different material. It may be desired that the straps be formed of an elastomeric material and stretchable.

The straps may comprise separate strap members having an end attached to the underside of the drape sheet. In an alternate embodiment, the straps may be defined by a continuous strap member that is attached to the underside of the sheet generally at a central location of the continuous strap, wherein opposite end sections of the continuous strap member define the laterally extending pair of straps.

The drape is also not limited by the number of strap pairs. The drape may include two or more pairs of the straps located at positions to restrain different parts of the patient. For example, one pair of straps may be provided to extend across and secure the patient's legs. Another pair of straps may be provided to extend across and secure the patient's torso, or head, or other body part. Pairs of the straps may be provided at opposite sides of a surgical site. For example, a pair of straps may be provided at opposite longitudinal ends of a fenestration defined in the drape. If an adhesive tape is provided on the underside of the drape for adhering the drape to the patient, the straps may be attached to the drape at locations outward of the adhesive so as not to interfere with the sterile field established by the tape.

To further aid in securing the patient, an embodiment of the drape may include an additional limb restraining device configured with the drapes. This device may be, for example, an additional tie device, such as a relatively short strip of material or belt member, attached to the straps at a location to encircle the patient's limb when the strap is properly drawn across the patient. For example, a tie device may be provided on each strap that is configured to encircle and secure the patient's leg. Likewise, ties may be provided for engaging the patient's arms. It should be appreciated that any manner of tie, belt, loop, or other adjustable device may be utilized for this purpose. This configuration may be desired in that undesired movement of the restrained limb is also prevented by use of the restraining straps.

Surgical drapes are typically provided in a folded form wherein they are placed on or above the patient prior to unfolding in multiple directions. It is desirable that the straps be accessible and secured around the patient prior to the unfolding procedure. In this regard, the straps may be attached at a location on the underside of the drape such that they are accessible in the folded configuration of the drape. In one embodiment, the straps may be attached to opposite sides of a longitudinal centerline of the drape and between adjacent fold lines, wherein the fold lines define an outer panel of the drape in its folded configuration. It should be appreciated that the arrangement of folds and strap attachment locations may be modified to provide ready access to the straps prior to unfolding the drape over the patient.

DETAILED DESCRIPTION

Reference will now be made in detail to one or more embodiments of the invention, examples of which are graphically illustrated in the drawings. The embodiments are provided by way of explanation of the invention, and not meant as a limitation of the invention. For example, features illustrated or described as part of one embodiment may be utilized with another embodiment to yield still a further embodiment. It is intended that the present invention include these and other modifications and variations.

As used herein, "attach" or "attached" refers to the bonding, joining, adhering, connecting attaching, or the like, of two elements. Two elements may be considered attached together when they are bonded directly to one another or indirectly to one another, such as when each is directly attached to an intermediate element.

"Elastomeric" refers to a material or composite that can be extended or elongated by at least 25% of its relaxed length and that will recover, upon release of the applied force, at least 10% of its elongation. It is generally preferred that the elastomeric material or composite be capable of being elongated by at least 100%, and recover at least 50% of its elongation. An elastomeric material thus may be considered "stretchable" or "extensible."

"Nonwoven web" refers to a web that has a structure of individual fibers or filaments that are interlaid, but in an identifiable repeating manner. Nonwoven webs or fabrics have been formed from many processes known to those skilled in the art, such as meltblowing processes, spunbonding processes, bonded carded web processes, and so forth. The basis weight of nonwoven fabrics is usually expressed in ounces of material per square yard (osy) or grams per square meter (gsm), and the fiber diameters are usually expressed in microns.

Surgical drapes formed in accordance with the present invention can generally possess any of a variety of sizes and shapes, depending on the particular use of the drape and its desired properties. For example, certain surgical drape configurations are described in U.S. Pat. No. 6,055,987, which is incorporated herein by reference for all purposes. Features of conventional drapes are discussed generally herein, but need not be described in detail for a complete understanding of drapes incorporating the novel instrument holder straps according to the invention.

Figure 1:
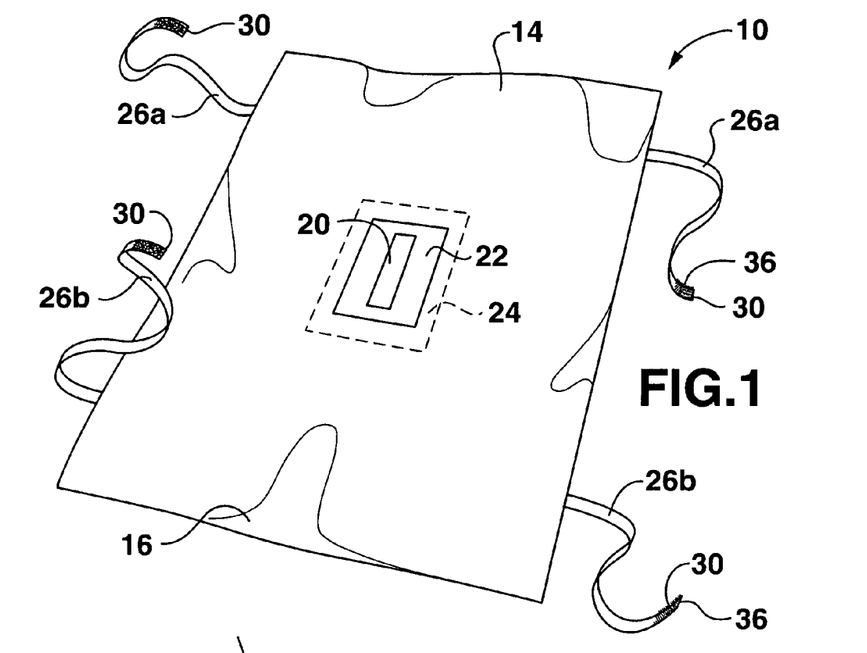
FIG. 1 is a perspective view of an exemplary embodiment of a surgical drape in accordance with the present invention, with two pairs of restraining straps.
Figure 2:
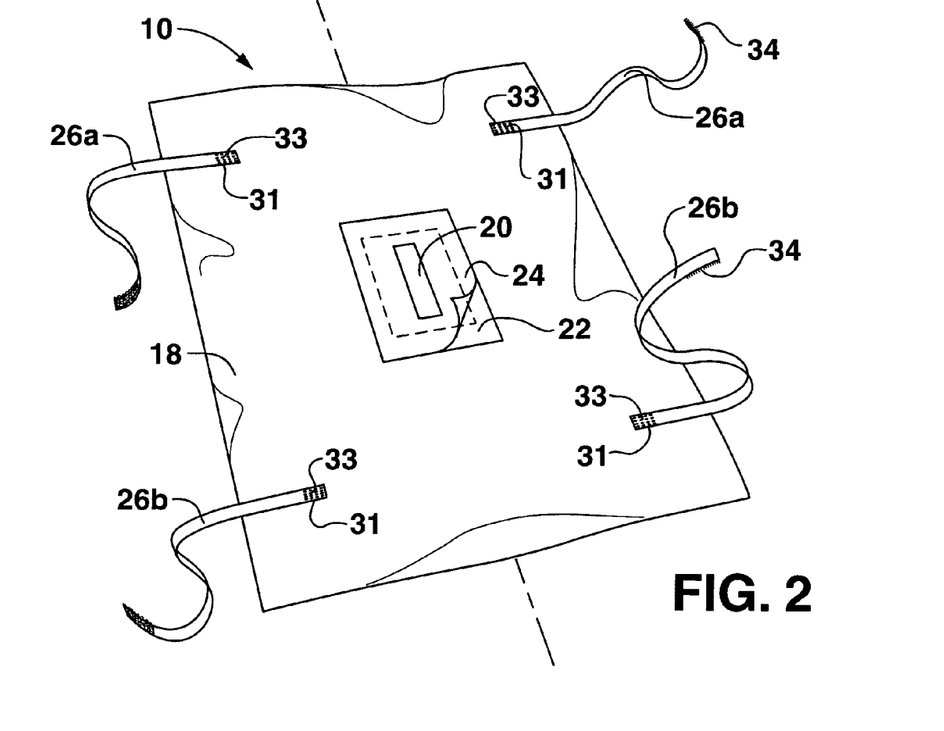
FIG. 2 is a perspective view of the exemplary embodiment of FIG. 1 taken from the underside of the drape.
Figure 3:
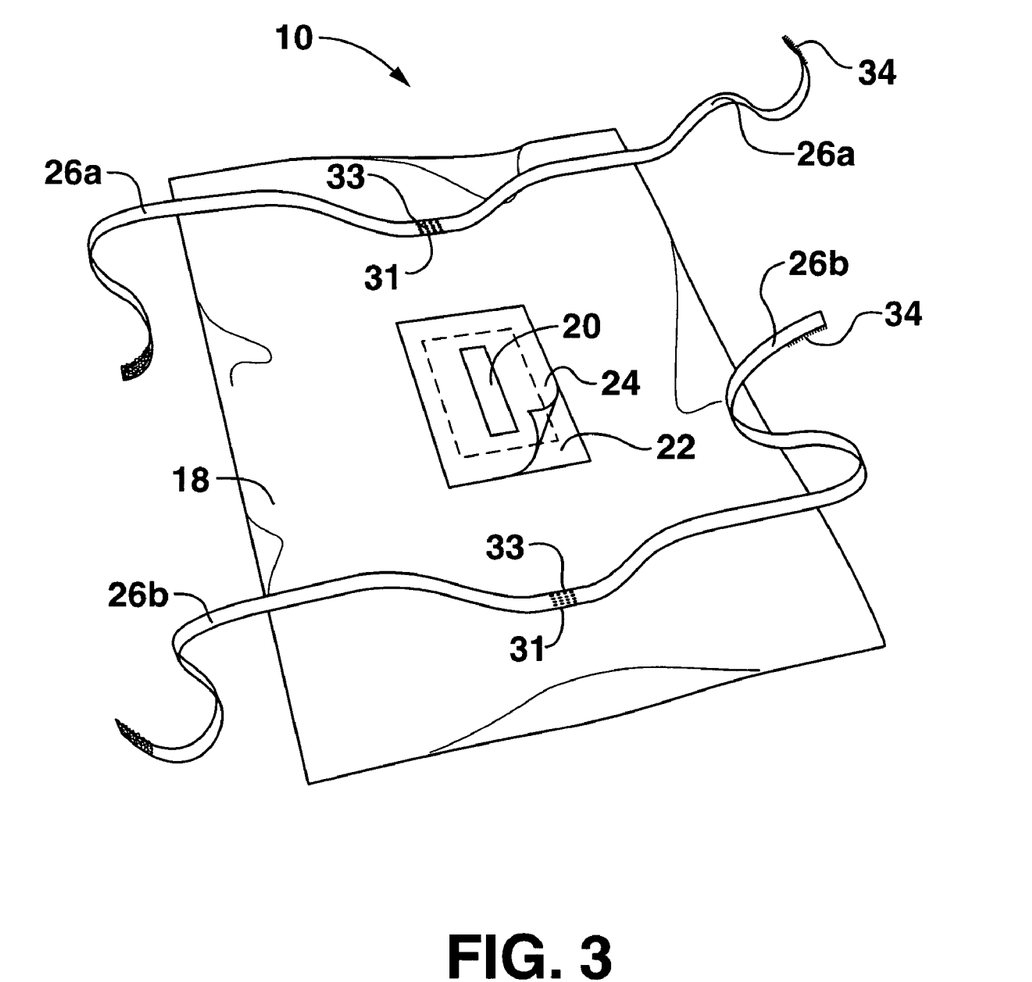
FIG. 3 is an underside perspective view of another exemplary embodiment of a drape according to the invention.

Referring to FIGS. 1-3, a surgical drape 10 is illustrated. The drape 10 includes a base sheet 14 having a top side 16 (away from the patient) and a bottom side 18 (towards the patient). The sheet 14 may be formed from one or more materials, for example one or more nonwoven layers, adhesive layers, film layers, and so forth. The sheet 14 may be hydrophilic or hydrophobic, and be chemically treated to achieve desired water absorbency properties. In a particular embodiment, the base sheet 14 may be a nonwoven surface layer joined to a barrier layer by a meltblown adhesive layer. The nonwoven surface layer may be a spunbond propylene material sheet with a basis weight of about 20 gsm and having been bonded by a repeating pattern of discretely fused spaced apart bonds. The meltblown adhesive layer may be made form an amorphous polyolefin applied to the spunbond material at a rate of, for example, 3 gsm. The barrier layer may be a polyethylene and calcium carbonate film of about 1.5 mils thick. The film is stretched in one direction prior to lamination to the spunbond by the meltblown adhesive layer. The film provides an impermeable barrier to aqueous fluids and alcohol solutions; the inclusion of the calcium carbonate and subsequent stretching improving moisture vapor permeability.

The drape 10 may include a fenestration opening 20 that is placed over the surgical site such that the surgical procedure is performed through the fenestration 20. The fenestration can have any desired shape and dimensions.

A separate material panel 22 may be attached to the base sheet 14 around the fenestration 20. This panel 22 may surround the fenestration 20, as illustrated in the figures, or be disposed along one or more sides of the fenestration 20. The panel 22 is generally referred to as a "reinforcement panel" and may have properties that differ from the base sheet 14. For example, the reinforcement panel 22 may be an absorbent multi-layered nonwoven fabric. One or more of the layers may be a film. The panel 22 may be hydrophilic or hydrophobic, and may be chemically treated to achieve a desired absorbency property. In a particular embodiment, the panel 22 is a spunbond layer attached to a middle layer of a meltblown material, which is further attached to a backing layer of impervious film. This configuration allows for the reinforcement of the areas around the fenestration 20, provides fluid absorption, and ensures a fluid impervious barrier.

The drape 10 may also include an adhesive area 24 on the bottom side 18 generally surrounding the fenestration 20. The adhesive area may be, for example, an adhesive tape that is used to attach the drape to the patient at the surgical site and establish a sterile field within the area defined by the tape, as is commonly understood in the art.

It should be understood that drape 10 may be formed entirely of the base sheet 14 without an additional reinforcement panel, or the drape 10 may be formed entirely of a material used for the reinforcement panel.

Figure 4:
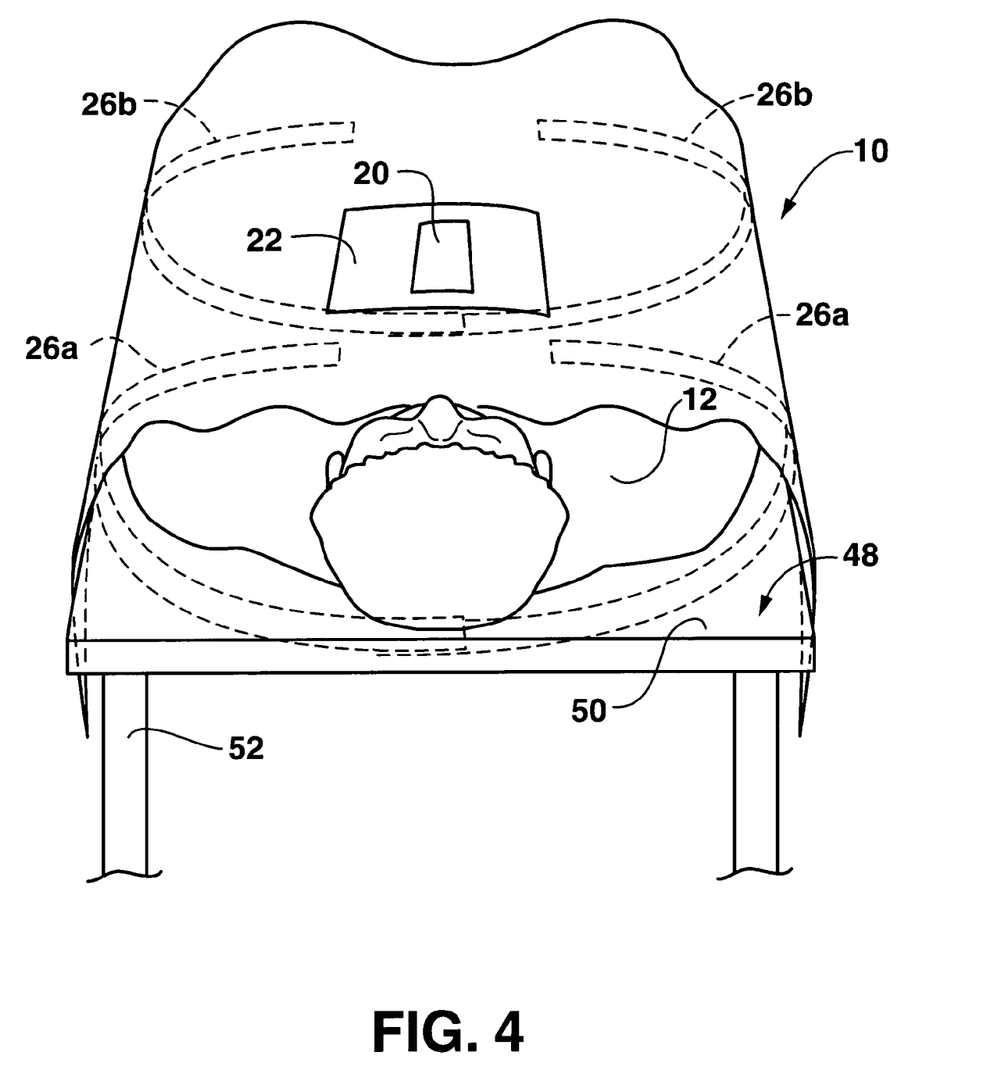
FIG. 4 is a perspective view of an embodiment of a drape according to the invention in use to retain a patient on a support surface.
Figure 5:
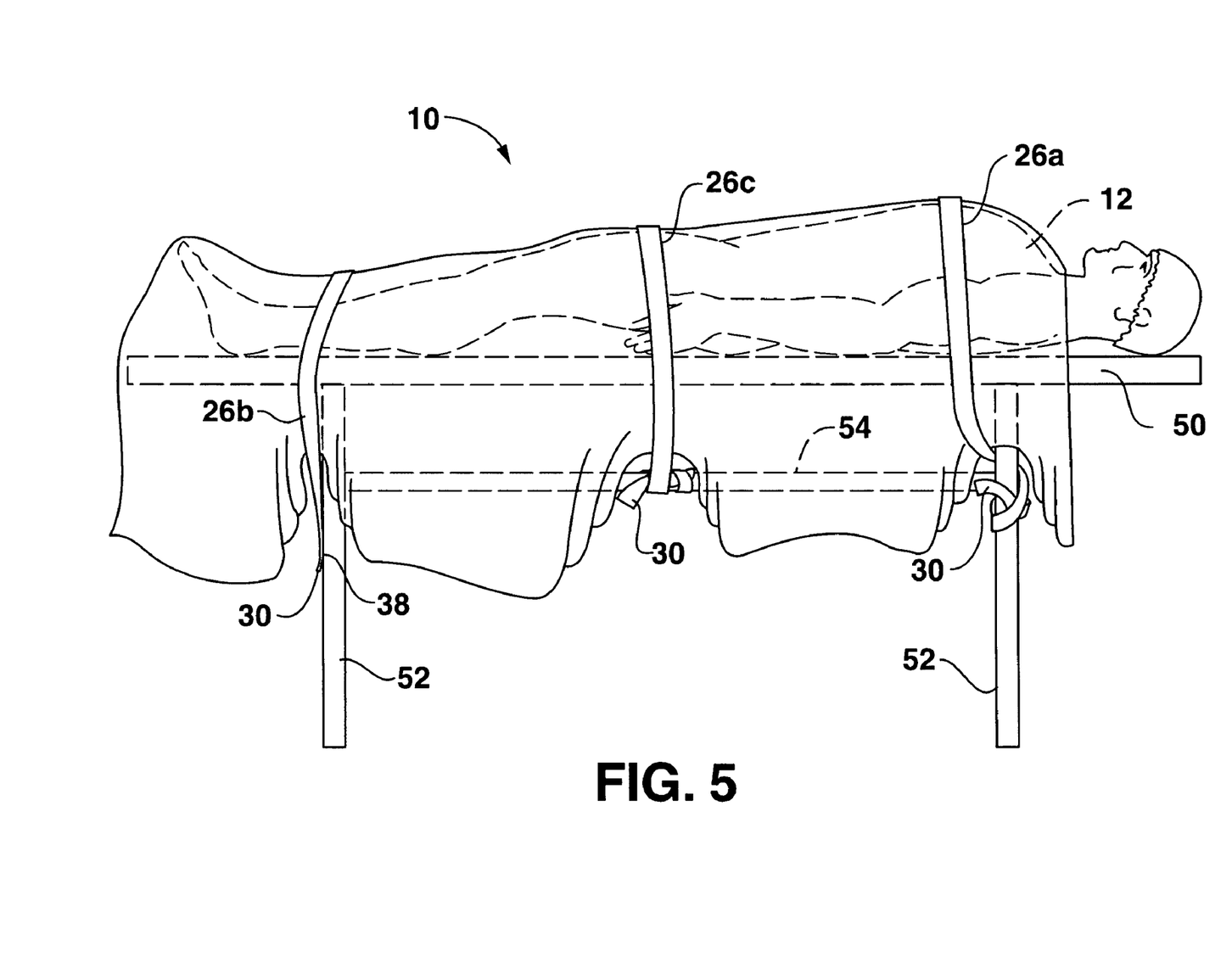
FIG. 5 is a cutaway perspective view of an embodiment of a drape according to the invention in use to retain a patient on a support surface.

At least one pair of straps, such as straps 26a, are configured on the underside 18 of the sheet 14. Alternatively, multiple pairs of the straps may be provided, including additional pair 26b. The straps are referred to collectively herein as "straps 26." The straps 26 have free ends 30 that extend in generally opposite directions laterally away from the sides of the sheet 14, as illustrated in the figures, and have a sufficient length so as to extend down below a support surface 48 upon which a patient 12 (FIG. 4) is resting, for example an operating table 50 as depicted in FIGS. 4 and 5. The straps 26 are intended to restrain the patient 12 in a desired position on the support surface 48, and to aid in preventing inadvertent patient movement during the procedure.

Figure 6:
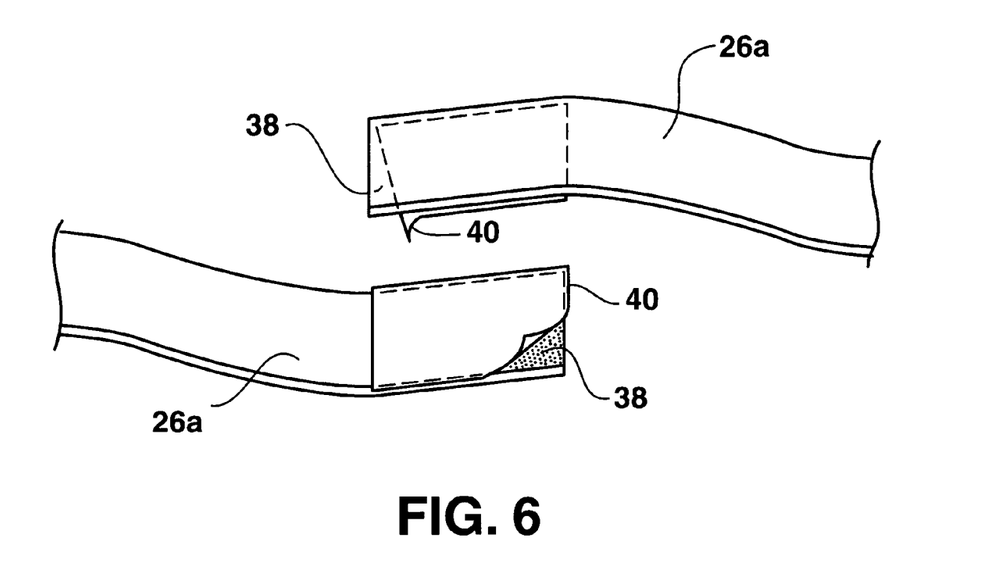
FIG. 6 is a perspective view of an exemplary attaching device, particularly an adhesive, which may be used with the restraining straps in accordance with the present invention.

In a particular embodiment, the straps 26 are configured to pass below the support surface 48 and attach together, as depicted in FIG. 4, thereby securing the patient 12 against the support surface 48. In this regard, any manner of conventional attaching device is provided on one or both of the free ends 30 of the straps 26 for securing the straps together. For example, the strap ends 30 may be secured together by conventional hook-and-loop material. Referring to FIGS. 1 and 2, a hook material 34 may be provide on an end section of the free end 30 of one strap 26, and a mating loop material 36 may be provided on an end section of the opposite strap 26. The loop material 36 may not be necessary if the straps 26 are formed of a material upon which the hook material 34 effectively attaches. Alternatively, the attaching device may be an adhesive 38 on one or both of the mating free ends 30 of the straps 26, as shown in FIG. 6. The adhesive 38 may be protected prior to use by a release liner 40 that is easily peeled from the adhesive 38 prior to attachment of the straps 26.

Figure 7:
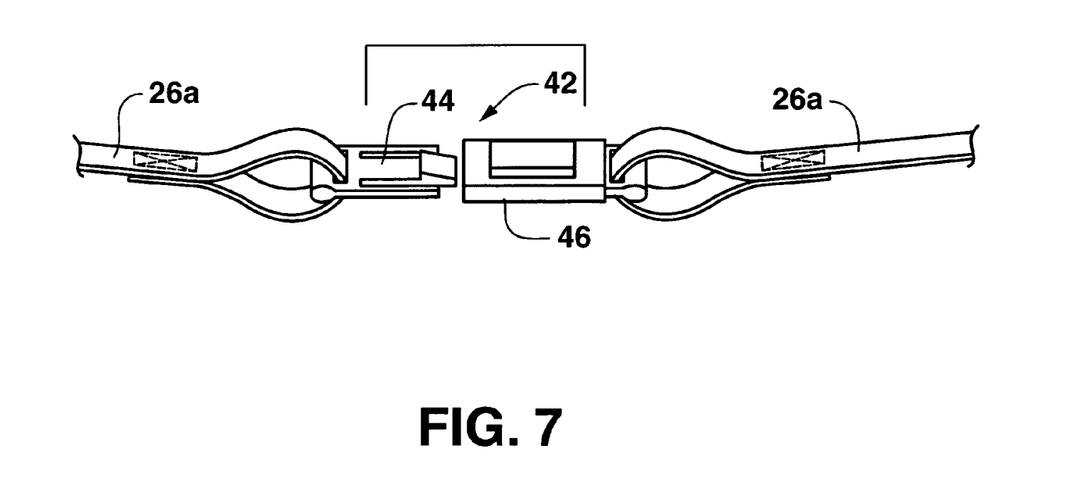
FIG. 7 is a perspective view of an exemplary type of mechanical attaching device that may be used with the restraining straps in accordance with the present invention.

FIG. 7 depicts a conventional mechanical fastener 42 having a male end 44 that inserts into a female end 46. The mechanical fastener 42 may allow for adjustability of the length of the strap free ends 30. Other suitable mechanical fasteners are well known, and all such devices are within the scope of the invention.

The attaching device may be as simple as having extended lengths of the straps 26 that can be tied together. It should be appreciated that the invention is not limited by the device or means by which the straps 26 may be secured to each other.

In an alternate embodiment as depicted in FIG. 5, the straps 26 are configured to restrain the patient 12 by attaching to one or more structural components of the support surface (operating table 50). In particular, the first pair of straps 26a are disposed over the patient's chest and are secured to a leg 52 of the table by wrapping around and being tied to the leg 52. A mechanical fastener such as a buckle, clip, or other device may be provided on the leg 52 for accepting and securing the straps 26a. Likewise, any manner of attaching device may be provided on the ends of the straps 26a. The second pair of straps 26b are disposed over the patient's legs and are secured to the leg 52 of the table by way of an adhesive 38. A third intermediate pair of straps 26c are disposed over the patient's midsection and are secured to a cross-support 54.

As mentioned, the straps 26 are not limited to any size, length, shape, or material. For example, the straps 26 may be formed of the same material as base sheet 14, or a different material. It may be desired that the straps 26 be formed at least in part of an elastomeric material and are thus stretchable.

The straps 26 may comprise separate strap members having an end 33 attached to the underside of the drape sheet 14, as depicted in FIG. 2. The ends may be attached at bond sites 31 using any conventional attaching method, such as welding, adhesives, sonic bonds, thermal bonds, stitching, and so forth. In an alternate embodiment, the straps 26 may be defined by a continuous strap member, as illustrated in FIG. 3. This continuous strap may be attached to the underside 18 of the sheet 14 generally at a central location of the continuous strap and sheet 14, wherein opposite end sections of the continuous strap member define the laterally extending pair of straps 26a.

As discussed, the drape 10 is not limited by the number of strap pairs. The drape may include two or more pairs of the straps located at positions to restrain different parts of the patient. In the illustrated embodiments, pairs of the straps 26 are provided at opposite longitudinal sides of a surgical site defined by the fenestration 20. If an adhesive tape 24 is provided on the underside 18 of the drape for adhering the drape to the patient, as illustrated in FIGS. 2 and 3, the straps 26 may be attached to the drape 10 at locations outward of the adhesive tape 24 so as not to interfere with the sterile field established by the tape.

Figure 10:
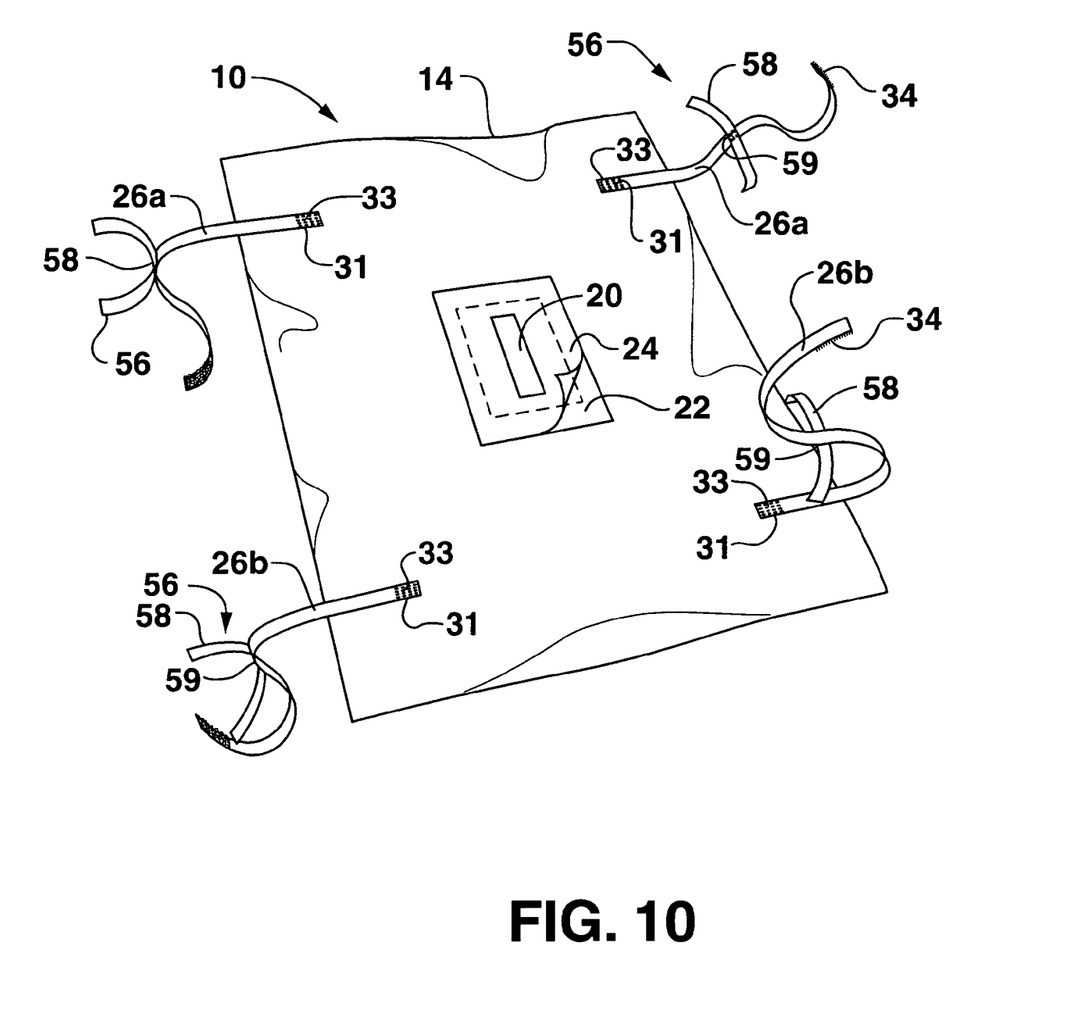
FIG. 10 is an underside perspective view of a drape embodiment according to the invention, particularly illustrating additional limb securing devices configured with the restraining straps.

FIG. 10 illustrates an embodiment of a drape 10 wherein additional limb restraining devices 56 are provided to further aid in securing the patient. The limb restraining devices 56 may be, for example, relatively short belts or strips of material that function as tie devices 58. The tie devices are attached to the straps 26 at a location to encircle the patient's limb when the strap 26 is properly drawn across the patient. For example, a tie device 58 may be provided on each strap 26 that is configured to encircle and secure the patient's leg. Likewise, tie devices 58 may be provided for engaging the patient's arms. It should be appreciated that any manner of tie, belt, loop, or other adjustable device may be utilized for this purpose. This configuration may be desired in that undesired movement of a patient's limb(s) is also prevented by use of the restraining straps 26.

Figure 8:
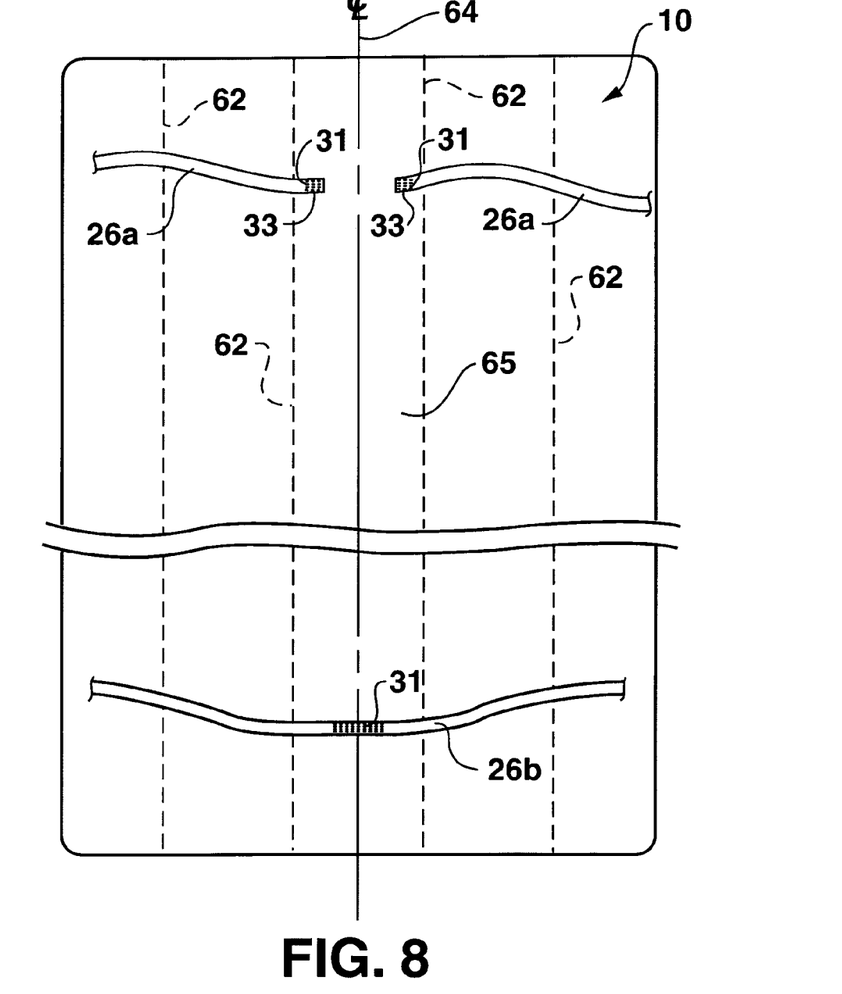
FIG. 8 is a view of the underside of a drape according to the invention particularly illustrating the fold lines and attachment locations of the restraining straps in one particular embodiment.
Figure 9:
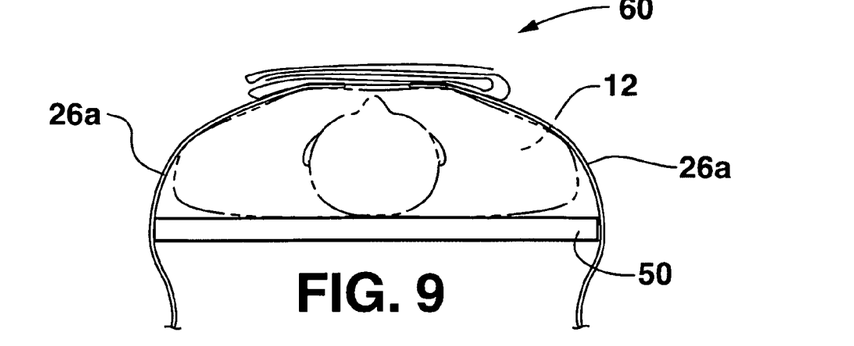
FIG. 9 is a perspective view of a folded drape according to the invention placed on a patient, particularly illustrating accessibility of the restraining straps prior to unfolding.

As described above, surgical drapes are typically provided in a folded form wherein they are placed on or above the patient prior to unfolding in multiple directions. The drapes 10 according to the invention may also be supplied in a folded compact configuration and it is desirable that the straps 26 be accessible and secured around the patient prior to the unfolding procedure. Although this may be accomplished in various ways, one solution is to attach the straps 26 to the underside 18 of the sheet 14 at a location that constitutes an exposed panel in the folded configuration of the drape. Referring to FIGS. 8 and 9, for example, the straps 26 are attached at a location on the underside 18 of the sheet 14 on opposite sides of a longitudinal centerline 64 of the drape and between adjacent fold lines 62. The panel 65 between the fold lines 62 is left exposed in the folding process such that the panels defined by fold lines outboard of lines 62 are folded onto the panel 65. The panel 65, with additional folds thereon, may then be folded multiple times to produce the configuration illustrated for example in FIG. 9. In this way, the straps 26 are accessible for securing around the patient 12 and/or to the operating table 50 prior to unfolding the drape 10 along the longitudinal fold lines illustrated in FIG. 8. It should be appreciated that multiple folding patterns and configurations are possible that will provide access to the straps 26, and all such configurations are within the scope and spirit of the invention.

It should be understood that the present invention includes various modifications that can be made to the exemplary embodiments of the surgical drape described herein as come within the scope of the appended claims and their equivalents.

What is claimed is:

1. A surgical drape for use during surgery on a patient, comprising:
    a sheet configured for covering at least a portion of the patient during surgery, said sheet having a top surface and an underside that is disposed against the patient in use of said drape, said sheet further comprising a fenestration through which a surgical procedure is performed;
    at least one pair of straps attached to said underside of said sheet at a location spaced from said fenestration so as not to be exposed through said fenestration, said straps extending in generally opposite directions laterally beyond sides of said sheet and having a sufficient length so as to secure the patient to a support surface upon which the patient is resting by extending below the support surface and engaging each other to pull the sheet and patient against the support surface;
    means for securing ends of said straps together, wherein said straps cooperate with said sheet to restrain the patient in a desired position relative to the support surface; and
    wherein said straps further comprise limb restraining devices configured to engage and secure one or more of the patient's limbs relative to said straps.

2. The surgical drape as claim 1, wherein said pair of straps comprise separate strap members attached to said underside of said sheet.

3. The surgical drape as in claim 1, wherein said pair of straps is defined by a continuous strap member secured to said underside of said sheet, said continuous strap having opposite end sections that define said laterally extending pair of straps.

4. The surgical drape as in claim 1, further comprising at least one additional pair of said straps, said pairs of straps spaced apart so as to be disposed on opposite sides of a surgical site.

5. The surgical drape as in claim 4, wherein said pairs of straps are disposed on opposite sides of said fenestration.

6. The surgical drape as in claim 1, further comprising an adhesive applied to said underside of said sheet for securing said sheet to the patient, said straps attached to said sheet at a location outward of said adhesive.

7. The surgical drape as in claim 1, wherein said means for securing comprises any combination of a hook and loop attachment provided on said ends of said straps, a mechanical fastening device, or an adhesive.

8. The surgical drape as in claim 1, wherein said limb restraining devices comprise adjustable tie devices attached to said straps.

9. The surgical drape as in claim 1, wherein said drape is in a folded configuration prior to use, said straps attached to said underside of said sheet at a location so as to be accessible for positioning over the patient and under said support surface prior to unfolding said drape.

10. The surgical drape as in claim 9, wherein said straps are attached to opposite sides of a longitudinal centerline of said drape and between adjacent fold lines.

11. A surgical drape for use during surgery on a patient, comprising:
    a sheet configured for covering at least a portion of the patient during surgery, said sheet having a top surface and an underside that is disposed against the patient in use of said drape;
    at least one pair of straps attached to an underside of said sheet at a location between a longitudinal end of said sheet and a surgical fenestration site in said sheet so as to lie over the patient without being exposed through said fenestration, said straps extending in generally opposite directions laterally beyond sides of said sheet and having a sufficient length so as to secure the patient to a support surface upon which the patient is resting by extending below said support surface and attaching to components of said support surface to pull said sheet and patient against said support surface; and
    wherein said straps further comprise limb restraining devices configured to engage and secure one or more of the patient's limbs relative to said straps.

12. The surgical drape as in claim 11, further comprising means for attaching ends of said straps to components of said support surface so that the patient is restrained in a desired position on said support surface by attaching said straps to said support surface.

13. The surgical drape as in claim 11, wherein said straps have a length so as to attach to each other below the support surface and pull said sheet and patient against the support surface, and further comprising means for attaching ends of said straps to each other below said support surface so that the patient is restrained in a desired position on said support surface by securing said ends of said straps together below said support surface.

14. The surgical drape as in claim 11, further comprising at least one additional pair of said straps, said pairs of straps spaced apart so as to be disposed on opposite sides of a surgical site defined in drape.

15. The surgical drape as in claim 11, wherein said straps comprise an elastomeric material.

16. The surgical drape as in claim 11, wherein said limb restraining devices comprise adjustable tie devices attached to said straps.

17. The surgical drape as in claim 11, wherein said drape is in a folded configuration prior to use, said straps attached to said underside of said sheet at a location so as to be accessible for positioning over the patient and down alongside said support surface prior to unfolding said drape.

18. The surgical drape as in claim 17, wherein said straps are attached to opposite sides of a longitudinal centerline of said drape.

* * * * *